United States Patent [19]

Kempe et al.

[11] Patent Number: 4,652,627

[45] Date of Patent: Mar. 24, 1987

[54] CALCITONIN ANALOGS WITH C-TERMINAL D-AMINO ACID SUBSTITUENTS

[76] Inventors: Tomas G. Kempe; Flora Chow, both of 16604 Windermere Pl., Minnetonka, Minn. 55345

[21] Appl. No.: 766,276

[22] Filed: Aug. 16, 1985

[51] Int. Cl.$^4$ .................... C07K 7/36; A61K 37/24
[52] U.S. Cl. .................................. 530/307; 514/808
[58] Field of Search ............... 260/112.5 T; 530/307; 514/808

[56] References Cited

U.S. PATENT DOCUMENTS 4,414,149 11/1983 Orlowski et al. ............ 260/112.5 T
4,469,632 9/1984 Orlowski et al. ............ 260/112.5 T

OTHER PUBLICATIONS

Lasmoles et al., *FEBS*, vol. 180, No. 1, 113–116 (1985).

Primary Examiner—Delbert R. Phillips
Attorney, Agent, or Firm—James R. Haller; Mary P. Bauman

[57] ABSTRACT

New calcitonin analogs are disclosed which have biological activity of the same type as known calcitonins and which have a D-amino acid substituent in at least one of the positions 31 and 32 instead of the natural L-amino acid units. The calcitonin analog may be analogs of salmon, eel, chicken, bovine, porcine, ovine, murine or human calcitonins.

11 Claims, No Drawings

CALCITONIN ANALOGS WITH C-TERMINAL D-AMINO ACID SUBSTITUENTS

FIELD OF THE INVENTION

This invention relates to calcitonin analogs having the ability to reduce the serum calcium concentration and to peptides which can be converted to calcitonin analogs having the ability to reduce the serum calcium concentration.

BACKGROUND OF THE INVENTION

Correlation of calcitonin structure to biological activity has proven difficult. Often the combination of single amino acid substitutions (ability to reduce level of serum calcium) has not resulted in additive effects on biological activity, perhaps due to a lack of information on the metabolic properties of the hormone. There is a wide variation in activity in the naturally occurring calcitonins with an approximate 40-fold range in biopotency. All calcitonins share some common structural features. Each is 32 amino acids long with a C-terminal prolinamide and an N-terminal disulfide linked ring from position 1 through 7. Salmon 1 calcitonin, for example, has the following formula (Niall, H. D. (1969) Proc. Natl. Acad. Sci. USA 64, 771–778):

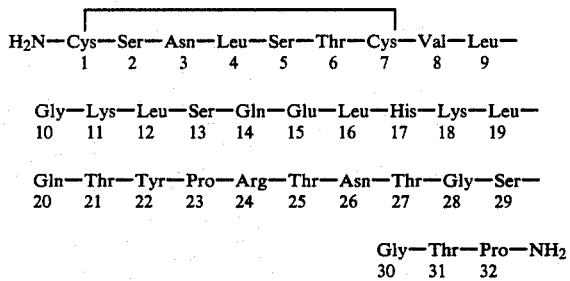

```
H2N—Cys—Ser—Asn—Leu—Ser—Thr—Cys—Val—Leu—
     1    2    3    4    5    6    7    8    9

Gly—Lys—Leu—Ser—Gln—Glu—Leu—His—Lys—Leu—
 10   11   12   13   14   15   16   17   18   19

Gln—Thr—Tyr—Pro—Arg—Thr—Asn—Thr—Gly—Ser—
 20   21   22   23   24   25   26   27   28   29

Gly—Thr—Pro—NH2
                               30   31   32
```

Other natural calcitonins have different degrees of homology with this sequence (Queener, S. F. and Bell, N. H. (1975) Metabolism 24, 555–567; Lasmoles, F. et al. (1985) FEBS Lett. 180, 113–116). The amino acid L-threonine (2S,3R configuration) at position 31 also occurs in eel, ovine, bovine, porcine and chicken calcitonins. The same position 31 is occupied by the amino acid L-alanine in human, murine and L-valine in salmon 2 calcitonin and salmon 3 calcitonin. Eel calcitonin differs from salmon 1 calcitonin by having the amino acids L-Asp at position 26, L-Val at position 27 and L-Ala at position 29.

Chicken calcitonin differs from salmon 1 calcitonin by having the amino acid L-Ala at position 2, L-Ser at position 3, L-Asp at position 26, L-Val at position 27 and L-Ala at position 29. Salmon 2 calcitonin differs from salmon 1 calcitonin by having L-Asp at position 15, L-Phe at position 22, L-Ala at position 29 and L-Val at position 31. Salmon 3 calcitonin differs from salmon 1 calcitonin by having L-Met at position 8, L-Asp at position 15, L-Phe at position 22, L-Ala at position 29 and L-Val at position 31.

The calcitonins of mammalian origin differ more markedly from salmon 1 calcitonin, as shown by the following comparison. The disulfide linkage between positions 1 and 7 is omitted from the following sequence for clarity.

| Position: | 1 | 2 | 3 | 4 | 5 | 6 | 7 |
|---|---|---|---|---|---|---|---|
| Salmon 1 | Cys | Ser | Asn | Leu | Ser | Thr | Cys |
| Human | " | Gly | " | " | " | " | " |
| Murine | " | " | " | " | " | " | " |
| Bovine | " | Ser | " | " | " | " | " |
| Porcine | " | " | " | " | " | " | " |
| Ovine | " | " | " | " | " | " | " |

| Position: | 8 | 9 | 10 | 11 | 12 | 13 | 14 |
|---|---|---|---|---|---|---|---|
| Salmon 1 | Val | Leu | Gly | Lys | Leu | Ser | Gln |
| Human | Met | " | " | Thr | Tyr | Thr | " |
| Murine | " | " | " | " | " | " | " |
| Bovine | Val | " | Ser | Ala | " | Trp | Lys |
| Porcine | " | " | " | " | " | " | Arg |
| Ovine | " | " | " | " | " | " | Lys |

| Position: | 15 | 16 | 17 | 18 | 19 | 20 | 21 |
|---|---|---|---|---|---|---|---|
| Salmon 1 | Glu | Leu | His | Lys | Leu | Gln | Thr |
| Human | Asp | Phe | Asn | " | Phe | His | " |
| Murine | " | Leu | " | " | " | " | " |
| Bovine | " | " | " | Asn | Tyr | " | Arg |
| Porcine | Asn | " | " | " | Phe | " | " |
| Ovine | Asp | " | " | " | Tyr | " | " |

| Position: | 22 | 23 | 24 | 25 | 26 | 27 | 28 |
|---|---|---|---|---|---|---|---|
| Salmon 1 | Tyr | Pro | Arg | Thr | Asn | Thr | Gly |
| Human | Phe | " | Gln | " | Ala | Ile | " |
| Murine | " | " | " | " | Ser | " | " |
| Bovine | " | Ser | Gly | Met | Gly | Phe | " |
| Porcine | " | " | " | " | " | " | " |
| Ovine | Tyr | " | " | " | " | " | " |

| Position: | 29 | 30 | 31 | 32 |
|---|---|---|---|---|
| Salmon 1 | Ser | Gly | Thr | Pro—NH2 |
| Human | Val | " | Ala | " |
| Murine | " | " | " | " |
| Bovine | Pro | Glu | Thr | " |
| Porcine | " | " | " | " |
| Ovine | " | " | " | " |

The structural features responsible for the increased potency of ultimobranchial calcitonins relative to calcitonins of mammalian origin have not yet been fully determined. The removal of the C-terminal amide group to a proline moiety in human calcitonin results in a drastic loss of the activity, from 100% to 0.06%. The deletion of the entire prolinamide moiety also gives a drastic loss in activity, from 100% to 0.12% (Rittel, W. et al. (1976) Experientia 32, 246–248).

U.S. Pat. No. 4,469,632 shows the replacement of naturally occurring Arg[24] with D-Arg[24] in salmon 1 calcitonin, with increased activity. On the other hand, U.S. Pat. No. 4,414,149 shows a reduction in activity of salmon 1 calcitonin when L-Val[8] and L-Arg[24] are respectively replaced with L-Gly[8] and D-Arg[24].

SUMMARY OF THE INVENTION

We have discovered that D-amino acid substituents at the C-terminal portion in synthetic salmon 1 calcitonin and other calcitonins provide calcitonin analogs having biological activity of the same type as known calcitonins (e.g., lowering plasma calcium levels). In our new peptides, the amino acid sequence contains at least one D-amino acid residue at position 31 or position 32 or both. The new peptides have good potency and quality when compared to known calcitonins. The introduction of D-amino acids which results in increased bioactivity can be due to increased stability and/or to specific structural features of the peptide analog.

The calcitonin analogs may be those of salmon, eel, chicken, bovine, porcine, ovine, murine or human. Preferably, a D-amino acid residue is at position 31 only. Preferred D-amino acid substituents are D-Ala, D-Val, D-Leu, D-Ile, D-Ser, D-Thr, D-Asp and D-Asn. A preferred analog is substituted salmon 1 calcitonin of the formula:

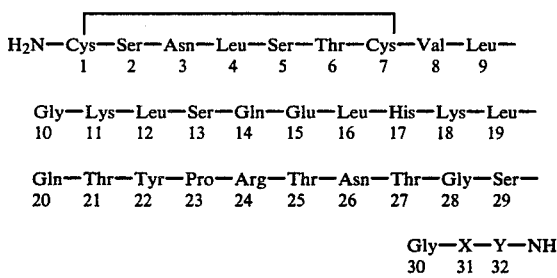

H₂N—Cys—Ser—Asn—Leu—Ser—Thr—Cys—Val—Leu—
     1    2    3    4    5    6    7    8    9

Gly—Lys—Leu—Ser—Gln—Glu—Leu—His—Lys—Leu—
10  11   12   13   14   15   16   17   18   19

Gln—Thr—Tyr—Pro—Arg—Thr—Asn—Thr—Gly—Ser—
20  21   22   23   24   25   26   27   28   29

Gly—X—Y—NH₂
30  31 32 in which X or Y or both are, independently, D-Ala, D-Val, D-Leu, D-Ile, D-allo-Ile, D-Ser, D-Thr, D-allo-Thr, D-Asp, D-Asn, D-Glu, D-Gln, D-Met, D-Met(SO), D-Met(SO₂), D-Pro, D-His, D-Phe, D-Tyr, D-Hypro, D-Lys, D-Arg, or the corresponding normally occurring L-amino acids, at least one of X or Y being a D-amino acid residue.

Preferred calcitonin analogs are [D-Ser³¹] calcitonin, [D-Thr³¹] calcitonin and [D-Asn³¹] calcitonin.

Particularly preferred peptides of the invention are the salmon 1 analogs, especially [D-Ser³¹] Salmon 1 calcitonin, [D-Thr³¹] Salmon 1 calcitonin and [D-Asn³¹] Salmon 1 calcitonin.

DESCRIPTION OF THE INVENTION

Resin Peptide Synthesis

The synthesis of calcitonin analogs may follow the stepwise solid phase strategy reported in Merrifield, R. B. (1963) J. Am. Chem. Soc. 85, 2149-2154, the teachings of which are incorporated herein by reference. The acid labile tert-butyloxycarbonyl (Boc-) group may be used for temporary alpha-N protection and the more acid stable groups may be used for protection of the side chains of the amino acids. Amino acid derivatives are listed in Table 1 and abbreviations are listed in Table 2. Attachment of the peptide chain to a copolymer matrix of styrene and 1% divinylbenzene may employ a benzhydrylamine type "handle" as reported in Pietta, P. G. et al. (1970) Chem. Commun. 650-651; Hruby, V. J. et al. (1977) J. Org. Chem. 42, 3552-3556; and Tam, J. P. et al. (1981) Tetrahedron Lett. 22, 2851-2854, which teachings also are incorporated by reference. All amino acids may be incorporated following a double coupling protocol with some modifications for particular amino acids. For all reactions, except for arginine, asparagine and glutamine, the first coupling employs the preformed symmetric anhydride method (Hagenmaier, H. and Frank, H. (1972) Hoppe-Seyler's Z. Physiol. Chem. 353, 1973-1976) in dichloromethane and the second coupling employs the preformed hydroxybenztriazole ester method (König, W. and Geiger, R. (1970) Chem. Ber. 103, 788-798) in dimethyl formamide (DMF). For Boc-Arg(Tos), standard DCC coupling conditions are employed to reduce the risk of lactam formation. The second coupling is done with the active HOBt ester method in DMF. Boc-Asn and Boc-Gln were exclusively coupled as HOBt esters in DMF to reduce nitrile and amidine formation (Mojsov, S. et al. (1980) J. Org. Chem. 45, 555-560). N-epsilon-(2-Chlorobenzyloxycarbonyl)lysine, Lys(ClZ), is used because it is more stable than the benzyloxycarbonyl derivative to the acid deprotection steps and it also avoids side chain branching (Erickson, B. W. and Merrifield, R. B. (1972) J. Am. Chem. Soc. 95, 3757-3763). The beta-cyclohexyl ester (cHex) of Boc-Asp-OH is used; it is also more stable to acids and thus minimizes aspartimide formation (Tam, J. P. (1979) Tetrahedron Lett. 4033-4036). The quantitative ninhydrin reaction is routinely used throughout the synthesis to monitor the extent of coupling after each cycle (Sarin, V. K. et al. (1981) Anal. Biochem. 117, 147-157).

TABLE 1

Amino acid derivatives for synthesis of salmon 1 calcitonin substitution analogs at position 31.

[D-Ser³¹]salmon 1 calcitonin

| cycl nr. and amino acid | protected amino acids | MW | mmol | g | coupling procedure |
|---|---|---|---|---|---|
| 32 | Pro—benzhydryl amine resin | | 1 | 2 | |
| 31 | Boc—D-Ser(Bzl) | 259.1 | 8 | 2.08 | A |
| | | | 4 | 1.04 | |
| 30,28,10 | Boc—Gly | 175.2 | 8 | 1.4 | A |
| | | | 4 | 0.7 | |
| 29,13,5,2, | Boc—Ser(Bzl) | 259.1 | 8 | 2.08 | A |
| | | | 4 | 1.04 | |
| 27,25,21,6 | Boc—Thr(Bzl) | 309.1 | 8 | 2.48 | A |
| | | | 4 | 1.24 | |
| 26,3 | Boc—Asn | 232.2 | 4 | 0.93 | B |
| 24, | Boc—Arg(Tos) | 442.5 | 4 | 1.77 | C |
| 23, | Boc—Pro | 215.1 | 8 | 1.72 | A |
| | | | 4 | 0.86 | |
| 22, | Boc—Tyr(Cl₂Bzl) | 441.2 | 8 | 3.53 | A |
| | | | 4 | 1.76 | |
| 20,14 | Boc—Gln | 246.3 | 4 | 0.98 | B |
| 19,16,12,9,4, | Boc—Leu | 249.2 | 8 | 2.0 | A |
| | | | 4 | 1.0 | |
| 18,11 | Boc—Lys(Cl—Z) | 314.8 | 8 | 2.5 | A |
| | | | 4 | 1.26 | |
| 17, | Boc—His(Tos) | 409.2 | 8 | 3.28 | A |
| | | | 4 | 1.64 | |
| 15, | Boc—Glu(OcHex) | 342.4 | 8 | 2.74 | A |
| | | | 4 | 1.37 | |
| 8, | Boc—Val | 217.1 | 8 | 1.74 | A |
| | | | 4 | 0.87 | |
| 7,1, | Boc—Cys(4-Me—Bzl) | 352.2 | 8 | 2.6 | A |
| | | | 4 | 1.3 | |
| [D-Thr³¹]salmon 1 calcitonin | | | | | |
| 31 | Boc—D-Thr(Bzl) | 309.1 | 8 | 2.48 | A |
| | | | 4 | 1.24 | |
| [D-Asn³¹]salmon 1 calcitonin | | | | | |
| 31 | Boc—D-Asn | 232.2 | 4 | 0.93 | B |

TABLE 2

Abbreviations (Biochem Biophys. Acta 133, 1-5 (1967))

Boc=tert-butyloxycarbonyl
Bzl=benzyl
Tos=tosyl
Cl₂Bzl=2,6-dichlorobenzyl
Cl-Z=o-chlorobenzyloxycarbonyl
OcHex=gamma-cyclohexyl ester
4-Me-Bzl=4-methylbenzyl
HOBt=N-hydroxybenztriazole
DIEA=diisopropylethylamine
DCC=dicyclohexylcarbodiimide
DMF=N,N-dimethylformamide
CM=carboxymethyl
TFA=trifluoroacetic acid
HPLC=high performance liquid chromatography
MRC units=Medical Research Council units standard
Pro=L-prolyl
Ser=L-seryl
Gly=L-glycyl Thr=L-threonyl
Asn=L-asparaginyl
Arg=L-arginyl
Tyr=L-thyronyl
Gln=L-glutaminyl
Leu=L-leucyl
Lys=L-lysyl
His=L-histidyl
Glu=L-glutaminyl
Val=L-valyl
Cys=L-cysteinyl
D-Ser=D-seryl
D-Thr=D-threonyl
D-Asn=D-asparaginyl Resin Peptide Cleavage and Purification Cleavage of the peptides from the resin and removal of all the remaining protecting groups is accomplished by treatment with anhydrous hydrogen fluoride in the presence of anisole (Yamashiro, D. and Li, C. H. (1978) J. Am. Chem. Soc. 100, 5174–5179). Crude peptide is removed from the resin by washing with 10% aqueous acetic acid. After lyophilization, the residue may be treated with dithiothreitol (Cleland, W. W. (1964) Biochemistry 3, 480–482) in sodium phosphate buffer at pH 7.5. The intramolecular disulfide bond in calcitonin between cysteine residues 1 and 7 can be formed by diluting the solution several-fold and adding potassium-ferricyanide in aqueous solution. The resultant peptide solution is then concentrated by passing it through a CM-Sephadex, C-25 column and then eluting with a linear gradient of sodium chloride from zero to 0.3 molar in the same phosphate buffer (Live, D. H. et al. (1977) J. Org. Chem. 42, 3556–3561; Moe, G. R. and Kaiser, E. T. (1985) Biochemistry 24, 1971–1976). The sample is finally desalted by gel filtration, concentrated and isolated by HPLC.

While the D-amino acid substitutions in at least one of the positions 31 and 32 may be made in salmon, eel, chicken, bovine, porcine, murine, ovine and human calcitonin, for exemplification, the following detailed disclosure is directed to salmon 1 calcitonin. The formula for our new substitution analogs at position 31 and position 32 of salmon 1 calcitonin may be written as follows:

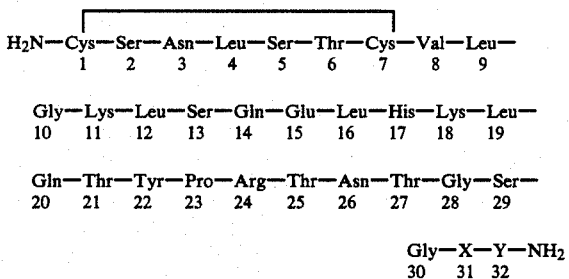

in which
X=D-Ala, D-Val, D-Leu, D-Ile, D-allo-Ile, D-Ser, D-Thr, D-allo-Thr, D-Asp, D-Asn, D-Glu, D-Gln, D-Met, D-Met(SO$_2$), D-Met(SO,), D-Pro, D-Hypro, D-Lys, D-Arg, D-His, or the corresponding L-amino acids; and
Y=D-Pro, D-Hypro, D-Phe, D-Tyr or the corresponding L-amino acids. At least one of X and Y is a D-amino acid residue.

As may be seen from the formula above, 32 amino acids are involved and in this formula, the positions are numbered according to the accepted procedure beginning at position 1 for the cysteine on one end of the chain and ending with proline amide at position 32 at the other end of the chain. For clarity of description, this same numbering system will be followed in referring to the cycles of the synthesis. The assembly of the amino acids begins with cycle 31 which involves the coupling of the amino acid to the proline moiety, followed by residue 30 and so on to the last amino acid. Protected amino acid derivatives that may be used in the synthesis of calcitonin analogs are given in Table 1. The resin which is functionalized with proline is available from chemical supply houses.

As indicated earlier, three types of coupling procedures are used, depending on the properties of reactants. In Table 1, the amino acid position and cycle number, type of coupling procedure, molecular weights and amount of reactants for the cycle are given. The details for each coupling protocol A, B and C are described below.

RESIN PEPTIDE SYNTHESIS

EXAMPLE 1

[D-Ser$^{31}$]salmon 1 calcitonin: Double coupling protocol using symmetric anhydride and active ester methods may be used to ensure as complete coupling as possible. The following protocol may be used for all amino acids except for arginine, asparagine and glutamine. The protocol is given for 2 g benzhydryl type resin functionalized with a total of 1 mMol of proline.

COUPLING PROCEDURE A

1. The resin is washed with dichloromethane, CH$_2$Cl$_2$, (30 mL, 6×1 min).
2. Removal of the Boc protecting group is done with 50% TFA in CH$_2$Cl$_2$ (30 mL, 3×1 min) and with 30 mL for 20 min.
3. The reagent is then removed with CH$_2$Cl$_2$ wash (30 mL, 6×1 min).
4. Traces of acid are finally removed with 5% DIEA in CH$_2$Cl$_2$ (30 mL, 2×2 min).
5. A final wash is done before the coupling is completed, CH$_2$Cl$_2$ (30 mL, 6×1 min).
6. 5 mg of the resin are removed for ninhydrin test.
7. The protected amino acid (listed in Table 1, 8 mMol) dissolved in 10 mL of CH$_2$Cl$_2$ is treated with DCC (4 mMol, 825 mg) in 3 mL of CH$_2$Cl$_2$. After 10 min, the solution is filtered and added to the resin. The precipitate is washed with 10 mL of CH$_2$Cl$_2$ and added to the reaction vessel which is then shaken for 2 h at room temperature.
8. The resin is washed with CH$_2$Cl$_2$ (30 mL, 4×2 min).
9. The resin is washed with 5% DIEA in CH$_2$Cl$_2$ (30 mL, 2 min).
10. The resin is washed with CH$_2$Cl$_2$ (30 mL, 4×2 min).
11. Ninhydrin test is performed.
12. The resin is washed with DMF (30 mL, 2×2 min).
13. HOBt (4 mMol, 540 mg) in 7 mL of DMF at 0° C. is mixed with DCC (4 mMol, 825 mg) in 3 mL CH$_2$Cl$_2$. The protected amino acid (listed in Table 1, 4 mMol) dissolved in 6 mL of DMF is then added. The mixture is kept for 10 min at 0° C. and is then added to the resin. The mixture is shaken for 2 h at room temperature.
14. The resin is then washed with DMF (30 mL, 2×2 min).
15. The resin is washed with $CH_2Cl_2$ (30 mL, 4×1 min).
16. The resin is washed with 5% DIEA in $CH_2Cl_2$ (30 mL, 2 min).
17. The resin is washed with $CH_2Cl_2$ (30 mL, 3×1 min).
18. Ninhydrin test is performed.

COUPLING PROCEDURE B (Used for the amino acids asparagine and glutamine)

Steps 1–6 were the same as coupling procedure A.
7. The resin is washed with DMF in $CH_2Cl_2$ (1:2 v/v, 30 mL, 2×2 min).
8. To HOBt (4 mMol, 540 mg) in 7 mL DMF/$CH_2Cl_2$ (1:1 v/v) at 0° C. is added DCC (4 mMol, 825 mg) in 3 mL of $CH_2Cl_2$. To that mixture is then added the protected amino acid (listed in Table 1, 4 mMol) in 6 mL of DMF/$CH_2Cl_2$. The reaction mixture is added to the resin after 10 min at 0° C. The resin is then shaken for 2 h at room temperature.
9. The resin is washed with DMF/$CH_2Cl_2$ (1:2 v/v, 30 mL, 2×2 min).

The steps 8–18 described in coupling procedure A are then followed.

COUPLING PROCEDURE C (Used for the amino acid arginine)

Steps 1–6 are the same as coupling procedure A.
7. The protected amino acid (listed in Table 1, 4 mMol) in 10 mL $CH_2Cl_2$ is added to the resin. DCC (4 mMol, 825 mg) in 3 mL $CH_2Cl_2$ is added after 5 min to the resin. The reaction mixture is then shaken for 2 h at room temperature.

The steps 8–18 described in coupling procedure A are then followed.

EXAMPLE 2

[D-Thr$^{31}$] salmon 1 calcitonin: The synthesis of this analog follows the same protocol as previously described for [D-Ser$^{31}$]salmon 1 calcitonin (Table 1). Boc-D-Thr(Bzl) is used in cycle 31 in the coupling to the proline residue linked to the resin. Coupling procedure A is used. The preceeding coupling reactions of residue 30 to 1 are the same as described previously for [D-Ser$^-$]salmon 1 calcitonin.

EXAMPLE 3

[D-Asn$^-$]salmon 1 calcitonin: Boc-D-Asn is used in cycle 31, and coupling procedure B is employed. The preceding couplings were the same as previously described (Table 1).

In each example, the addition of Cys$^1$ represents the completion of the solid phase synthesis. The Boc group is finally removed by steps 1–6 in coupling procedure A. The resin peptides are then removed from the reaction vessel and dried in vacuum. Cleavage and purification steps are carried out as follows:

RESIN-PEPTIDE CLEAVAGE

The dried resin peptide (2 g) and 2 mL of anisole are placed in a teflon reaction vessel which is cooled in a dry ice-acetone bath and about 15 mL of hydrogen fluoride gas is condensed into the vessel. The mixture is stirred at 0° C. in an ice bath for 45 min. The hydrogen fluoride is then evaporated under vacuum, using first a water aspirator and later a high vacuum pump. The residue is triturated with 5×30 mL of ethyl acetate, and the peptide was extracted from the resin beads with 100 mL of 10% aqueous acetic acid solution. The mixture was lyophilized to dryness.

PURIFICATION OF CRUDE PEPTIDES

A 100 mg sample of the lyophilized peptide is treated with excess dithiothreitol (5 mMol) in 5 mL of 50 mM sodium phosphate buffer at pH 7.5 for 1 h at room temperature. The intramolecular disulfide bond between cysteine residues 1 and 7 is formed by diluting the peptide solution to a volume of 1 liter in the same buffer. A solution of 20 mM $K_3Fe(CN)_6$ is slowly added with stirring until a persistant yellow color is obtained. The resultant dilute peptide solution is concentrated by passing it through a CM-Sephadex, C-25 column and then eluting with a linear gradient of NaCl from zero to 0.3M employing the same buffer. Fractions from this column may be desalted on a Sephadex G-15 column, eluting with a 0.03M aqueous acetic acid solution. Samples for biological testing are isolated on an analytical HPLC (column: Altex ODS, 5 micron, 4.6×250 mm, flow 1.5 mL/min, gradient of 30–45% acetonitrile in 0.1M ammonium acetate buffer at pH 5.5). The isolated samples may be quantified using salmon 1 calcitonin as reference sample.

The HPLC isolated samples are hydrolyzed with 5.5M hydrochloric acid, and amino acid analyses are performed to confirm the chemical composition.

The new polypeptides are useful in lowering the content of calcium in the plasma, as indicated by standard tests in rats (Kumar, M. A. et al. (1965) J. Endocrinology 33, 469–475). While only certain embodiments of our invention have been described in specific details, it will be apparent to those skilled in the art that many other specific embodiments may be practiced and many changes may be made, all within the spirit of the invention and the scope of the appended claims.

What is claimed is:

1. A biologically active calcitonin having 32 amino acid residues with a C-terminal amide and a N-terminal disulfide linked ring from position 1 through 7 and having a D-amino acid substituent at position 31 or position 32 or both.

2. The compound of claim 1 wherein the D-amino acid substituent is D-Ala, D-Val, D-Leu, D-Ile, D-Ser, D-Thr, D-Asp, D-Asn, D-Glu, D-Gln, D-Met, D-Met(SO), D-Met(SO$_2$), D-Pro, D-Hypro, D-Lys, D-Arg, D-His, D-Phe or D-Tyr.

3. The compound of claim 1 wherein the calcitonin is [D-Ser$^{31}$]salmon 1 calcitonin.

4. The compound of claim 1 wherein the calcitonin is [D-Thr$^{31}$]salmon 1 calcitonin.

5. The compound of claim 1 wherein the calcitonin is [D-Asn$^{31}$]salmon 1 calcitonin.

6. The compound of claim 1 wherein the calcitonin is salmon, eel, chicken, bovine, porcine, ovine, murine or human calcitonin.

7. A biologically active calcitonin having 32 amino acid residues with a C-terminal prolinamide and a N-terminal disulfide linked ring from position 1 through 7 and having a D-amino acid substituent at position 31.

8. The calcitonin of claim 7 in which the D-amino acid substituent is D-Ala, D-Val, D-Leu, D-Ile, D-Ser, D-Thr, D-Asp or D-Asn.

9. [D-Ser$^{31}$] calcitonin.

10. [D-Thr$^{31}$] calcitonin.

11. [D-Asn$^{31}$] calcitonin.

* * * * *